Nov. 11, 1975 C. MEYER Plant Pat. 3,802
ROSE PLANT-BICENTENNIAL VARIETY
Filed Oct. 7, 1974
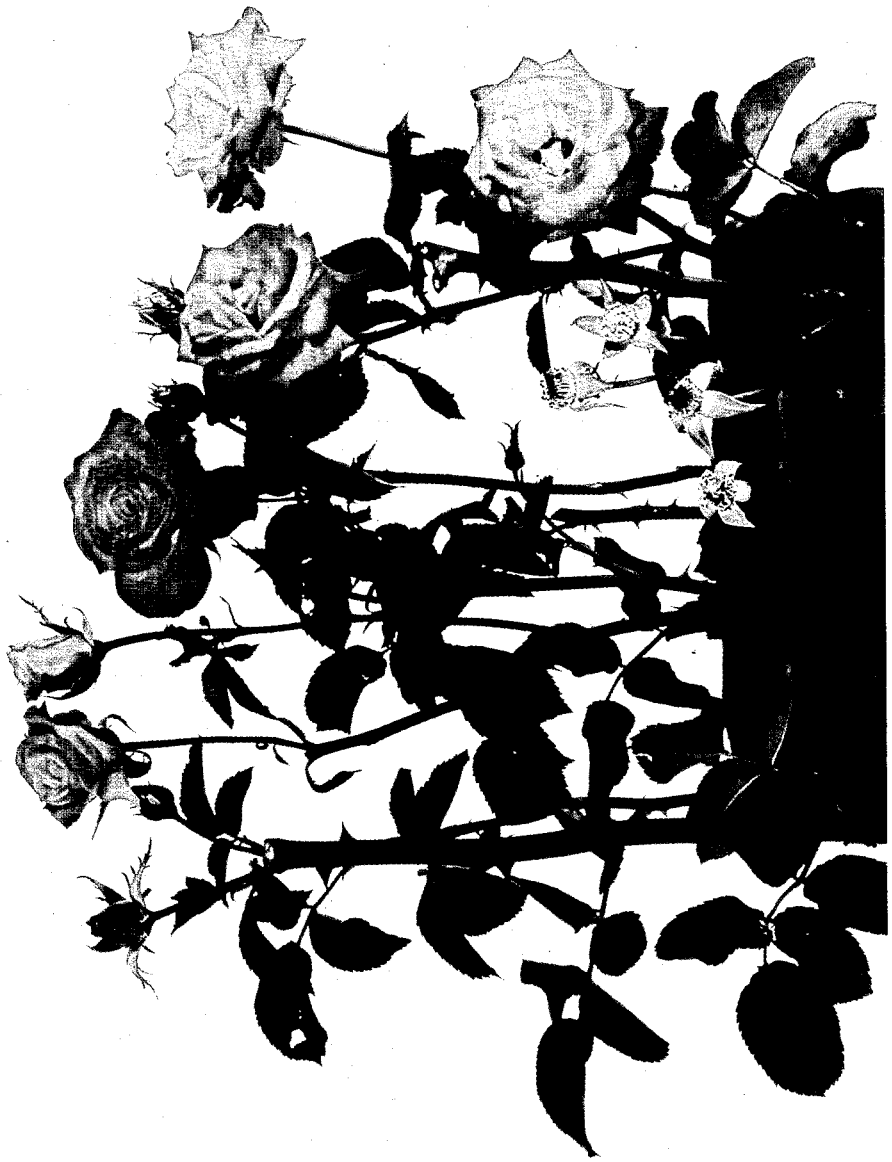

United States Patent

Plant Pat. 3,802

Patented Nov. 11, 1975

3,802

ROSE PLANT—BICENTENNIAL VARIETY

Carl Meyer, Cleves, Ohio, assignor to The Conard-Pyle Company, West Grove, Pa.

Filed Oct. 7, 1974, Ser. No. 512,433

Int. Cl. A01h 5/00

U.S. Cl. Plt.—22 1 Claim

ABSTRACT OF THE DISCLOSURE

A new and distinct variety of rose plant of the floribunda class, originated by crossing Pink Parfait (Plant Pat. No. 1,904) with Granada (Plant Pat. No. 2,214).

SUMMARY OF THE INVENTION

The present invention relates to a new and distinct variety of rose plant of the floribunda class which was originated by me by crossing the variety Pink Parfait (Plant Pat. No. 1,904) with the variety Granada (Plant Pat. No. 2,214).

My objective in this breeding and in making this cross was to produce a new and improved rose variety of superior habit of growth, color combination different from all other varieties, and unique regular flower form. I was successful in my objective as evidenced by the following combination of characteristics which are outstanding in my new rose:

1. A plant of compact growth and very freely branched.
2. A habit of growth of even, regular form and a neat, well balanced appearance.
3. A floriferous plant producing good quantities of flowers both singly and several to a stem continuously through the growing season.
4. Flowers of uniform size, petals arranged regularly and many with a prominent tooth at the petal tip.
5. A distinctive combination of brilliant red color at the petal margins where touched by the sun, blending to lighter red shades toward the base of the petal.
6. Foliage of medium size, abundant, heavy and leathery, and of pleasing medium green color.

This rose differs from its seed parent Pink Parfait (Plant Pat. No. 1,904) by its brilliant red color at the petal margins where touched by the sun and lighter red toward the base of the petal, unique form and a prominent tooth at the tip of most petals, low compact growth habit, its darker green foliage and stiff stems.

As compared to its pollen parent Granada (Plant Pat. No. 2,214), it differs by its unique combination of brilliant red at the petal margin where touched by the sun and lighter red toward the base of the petal, its regular form, it is less fragrant, and more freely branched with more balanced habit of growth.

Asexual reproduction of the new variety by budding as performed at West Grove, Pa., and Cleves, Ohio, showed the characteristics and distinction come true to form and are established and transmitted through succeeding propagations.

BRIEF DESCRIPTION OF DRAWING

The accompanying drawing shows typical specimens of the vegetative growth and flowers of my new variety in different stages of development as depicted in color as nearly true as it is reasonably possible to make the same in a color illustration of this character.

DETAILED DESCRIPTION OF DISCLOSURE

The following is a detailed description of the new variety with color terminology in accordance with the Royal Horticultural Society Color Chart:

Type: Hardy; bush; seedling; for garden decoration.
Class: Hybrid, floribunda.

Propagation: It does hold its distinguishing characteristics through succeeding propagations by budding.

FLOWER

Locality where grown: West Grove: Pa.
Flowers borne: Singly and several to stem; in irregular cluster; on normal medium long stems.
Quantity of bloom: Free, abundant, outdoors.
Continuity: Continuous.
Fragrance: Moderate; spicy.
Bud:

*Peduncle.*—Medium long; medium heavy; erect; medium green with a light reddish discoloration where touched by the sun; almost smooth; medium size; hairs; red brown.

*Before calyx breaks.*—Size: small. Form: Short pointed with a conspicuous neck; with foliaceous appendages on the surface of the bud; with medium thickness, much cut foliaceous parts extending beyond the tip of the bud equal to ⅓ of its length.

*As calyx breaks.*—Color: 53B.

*As first petal opens.*—Size: Medium. Form: Medium; cylindrical with petals laying together and opening uniformly rather than the outside petals rolling away from the petals of the inside rows. Color: Outside: 53C as the calyx breaks, deepening to 53A between sections of the calyx, becoming 160C at the base near point of attachment. Inside: 53C becoming 1D at the base near point of attachment.

*Opening.*—It does open up well in all normal weather conditions during the growing season at West Grove, Pa.

Bloom: Size when fully open: Medium, 6 cm. to 8 cm.

*Petalage.*—Double (more petals, but the stamens not hidden); from 29 to 31 petals with 5 to 7 additional petaloids; arranged regularly.

*Form.*—Flat high centered at first; becoming open high centered; petals remaining at first flat rolled outward; becoming later at maturity loosely rolled outward.

Petals: Medium; with inside satiny; outside somewhat shiny.

*Shape.*—Outer: Round with no notches. Intermediate: Round; with 1 prominent tooth. Inner: Ovate; with 1 tooth.

*Color.*—Colors may be modified by being shaded with other colors.

This description of a newly opened flower was made from a rose grown outdoors in August 1974, at West Grove, Pa.

*Color.*—Outer petal: Outside surface: The petal edge 59B, immediately becoming 58B. Inside surface: The outer edge more brilliant than 53A where touched by the sun, becoming 58B near the center where shaded by overlapping petals, becoming 2D at point of attachment. Intermediate petal: Outside surface: 63B becoming 2D at point of attachment. Inside surface: 53A on the outer edge where touched by the sun, becoming between 55A and 55B where shaded by overlapping petals, and becoming 1C at point of attachment. Inner petal: Outside surface: 61D, becoming 1D at point of attachment. Inside surface: 53A at the outer edge where touched by the sun, becoming 54B where shaded by overlapping petals and becoming 1C at point of attachment.

This description was made from a rose that was open for three days in August 1974, at West Grove, Pa.

*Color.*—Outer petal: Outside surface: 53C on upper part of petal, becoming 53D in mid part of petal and becoming 2D at point of attachment. Inside surface: 53A on upper part of petal, becoming 54B in mid part of petal, and becoming 2C at point of attachment. Inner petal: Outside surface: 54B, becoming 2D at point of attachment. Inside surface: 53A at edge of petals where touched by the sun, immediately becoming 58C near the center where shaded by overlapping petals, becoming 2C at the point of attachment.

General color effect:

*Newly opened flowers.*—55A, shading to 53A on the outer ¼ of the flower when viewed from directly above.

*Three days open.*—55A, shading to 53A at the edge of the flower when viewed from directly above.

Behavior: Sometimes persist; fading brown; flower usually drops clean at point where peduncle attaches to stem, as a result no seed hips have been observed on this rose.

Flower longevity: On bush 4 to 5 days in August outdoors, kept at living room temperatures 4 days in August.

REPRODUCTIVE ORGANS

Stamens: Many; arranged irregularly about pistils.

Filaments: Many; most with anthers; medium length. Color: 2C.

Anthers: All open at various times; medium size. Color: 15A. Seldom an anther fused with a petaloid or pistil.

Pollen: Moderate; gold.

Pistils: Many.

Styles: Uneven; medium to long; medium thickness; bunched.

Stigma: Whitish yellow.

Ovaries: All enclosed in receptacle.

Hips: None observed.

Sepals: Permanent; moderately long; recurved.

Seeds: None observed.

PLANT

Foliage:

*Leaves.*—Usually 5, occasionally 3 or 7 leaflets abundant; medium size; moderately heavy, leathery.

*Leaflets.*—Shape: ovoid with apex acute, base round, margin simply serrate.

*Color.*—Mature—Upper surface: 147A. Under surface: between 147B and 148B. Young—Upper surface: 187A. Under surface: 187B.

*Rachis (the supporting stem of the compound leaf)*: Medium weight. Upper side: Grooved prickly. Under side: Usually smooth with occasional prickle when fully matured.

*Stipules.*—Medium long; medium wide; medium long points; less than 45°.

*Disease.*—Resistance comparable to the average variety growing under the same cultural conditions.

Growth:

*Habit.*—Bushy, much branched.

*Growth.*—Very free.

*Canes.*—Medium.

*Main stems.*—Bright. Color: 144A. Prickles: several. Color: 166A. Hairs: None. Branches: Bright. Color: 144A. Prickles: Few. Color: 166B. Hairs: None. New shoots: Bright. Color: 147C. Prickles: Few. Color: 180C. Hairs: Few. Color: Indistinguishable.

I claim:

1. A new and distinct variety of rose plant of the floribunda class, substantially as herein shown and described, characterized particularly as to novelty by the unique combination of the red colors, with unique flower form, vigorous growth, medium flower size with bloom produced in abundance, and heavy leathery foliage.

No references cited.

ROBERT E. BAGWILL, Primary Examiner